(12) United States Patent
Asada et al.

(10) Patent No.: US 6,699,199 B2
(45) Date of Patent: Mar. 2, 2004

(54) PHOTOPLETHYSMOGRAPH SIGNAL-TO-NOISE LINE ENHANCEMENT

(75) Inventors: Haruhiko H. Asada, Lincoln, MA (US); Reginald C. Hutchinson, Malden, MA (US); Phillip Shaltis, Jackson, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/167,069

(22) Filed: Jun. 11, 2002

(65) Prior Publication Data

US 2002/0169381 A1 Nov. 14, 2002

Related U.S. Application Data

(63) Continuation-in-part of application No. 09/552,185, filed on Apr. 18, 2000, now Pat. No. 6,402,690.

(51) Int. Cl.[7] .................................................. A61B 5/02
(52) U.S. Cl. ........................ 600/504; 600/579; 600/481
(58) Field of Search ................................. 600/504, 505, 600/507, 473, 476, 479, 480, 300, 310, 561, 481, 587

(56) References Cited

U.S. PATENT DOCUMENTS

| | | | |
|---|---|---|---|
| 3,835,839 A | 9/1974 | Brown ........................ 128/2.05 |
| 3,878,502 A | 4/1975 | Rochelle ........................ 340/5 |
| 3,972,038 A | 7/1976 | Fletcher et al. ........ 340/189 M |
| 3,972,320 A | 8/1976 | Kalman ................... 128/2.1 A |
| 4,063,410 A | 12/1977 | Welling ........................ 58/38 R |
| 4,396,906 A | 8/1983 | Weaver ............... 340/347 DD |
| 4,509,528 A | * 4/1985 | Sahota ........................ 600/504 |
| 4,535,324 A | 8/1985 | Levental ..................... 340/574 |
| 4,539,997 A | 9/1985 | Wesseling et al. .......... 128/167 |
| 4,799,062 A | 1/1989 | Sanderford, Jr. et al. ... 342/450 |
| 4,825,872 A | 5/1989 | Tan et al. .................... 128/633 |
| 4,827,943 A | 5/1989 | Bornn et al. ................. 128/668 |
| 4,924,450 A | 5/1990 | Brashear et al. ............. 267/118 |
| 5,152,296 A | 10/1992 | Simons ........................ 128/670 |
| 5,285,784 A | 2/1994 | Seeker ........................ 128/633 |
| 5,297,548 A | 3/1994 | Pologe ........................ 128/633 |

(List continued on next page.)

FOREIGN PATENT DOCUMENTS

| | | |
|---|---|---|
| DE | 31 50925 | 6/1983 |
| DE | 3609 913 | 10/1987 |
| EP | 0 467 853 | 7/1991 |
| EP | 0706 776 | 4/1996 |
| EP | 0 724 860 | 8/1996 |
| FR | 1 655 834 | 6/1991 |
| WO | WO 93/16636 | 9/1993 |
| WO | WO 98/07172 | 2/1998 |
| WO | WO 98/17172 | 4/1998 |
| WO | WO 01/67946 | 9/2001 |

OTHER PUBLICATIONS

Asada et al. The Ring Sensor: a New Ambulatory Wearable Sensor for Twenty–Four Hour Patient Monitoring, Proceeding of the 20th Annual International Conference of the IEEE Engineering in Medicine and Biology Society, Hong Kong, Oct. 29–Nov. 1, 1998.

(List continued on next page.)

Primary Examiner—Max F. Hindenburg
Assistant Examiner—Navin Natnithithadha
(74) Attorney, Agent, or Firm—Bromberg & Sunstein LLP

(57) ABSTRACT

A ring plethysmograph having a pressure adjustment for locally pressurizing one side of a finger thereby biasing the pressure on an artery wall so that the plethysmograph is optimally sensitive without interfering with blood flow. An auxiliary photodetector, possibly with a second light source, is disposed on the low-pressure side of the finger for two purposes: providing a noise reference for canceling noise on the plethysmograph signal, and also for providing a separate motion signal for monitoring the activity level of a patient.

11 Claims, 5 Drawing Sheets

U.S. PATENT DOCUMENTS

| | | | |
|---|---|---|---|
| 5,309,916 A | 5/1994 | Hatschek | 128/672 |
| 5,511,546 A | 4/1996 | Hon | 128/633 |
| 5,638,818 A | 6/1997 | Diab et al. | 128/653.1 |
| 5,661,460 A | 8/1997 | Sallen et al. | 340/573 |
| 5,694,939 A | 12/1997 | Cowings | 128/671 |
| 5,735,800 A | 4/1998 | Yasukawa et al. | 600/503 |
| 5,738,102 A | 4/1998 | Lemelson | 128/671 |
| 5,771,001 A | 6/1998 | Cobb | 340/573 |
| 5,964,701 A | 10/1999 | Asada et al. | 600/300 |
| 6,263,222 B1 | 7/2001 | Diab et al. | 600/310 |
| 6,388,247 B2 | 5/2002 | Asada et al. | 250/221 |

OTHER PUBLICATIONS

Asada et al. Modeling of Finger Photoplethysmography for Wearable Sensors.

Asada et al. Artifact–Resistant Power–Efficient Design of Finger–Ring Plethysmographic Sensors, IEEE Transactions on Biomedical Engineering, vol. 48, No. 7, Jul. 2001.

Kamiya et al. Long–term ambulatory monitoring of indirect arterial blood pressure using a volume–oscillometric method, Med. & Biol. Eng. & Comput. 1985, 23, 459–465.

Yamakoshi et al. Current developments in non–invasive measurement of arterial blood pressure, J. Biomed.Eng., vol. 10, 129–137, 1988.

* cited by examiner

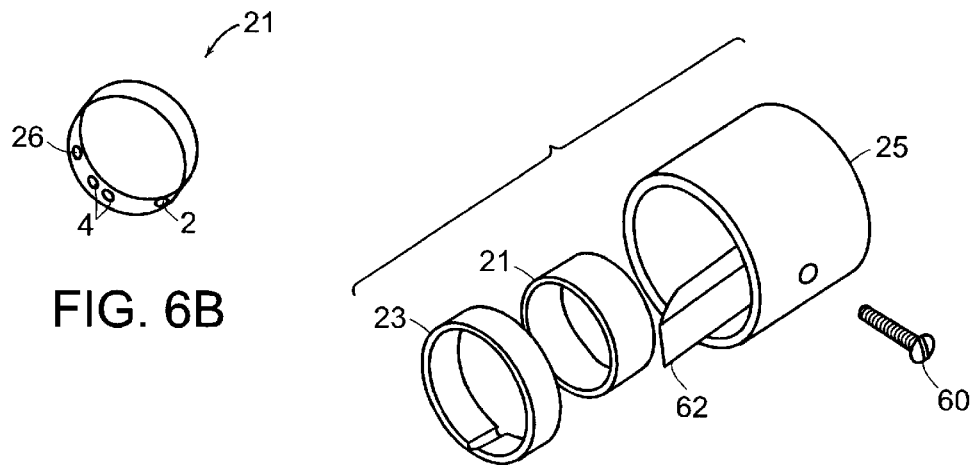
FIG. 6B
FIG. 6A
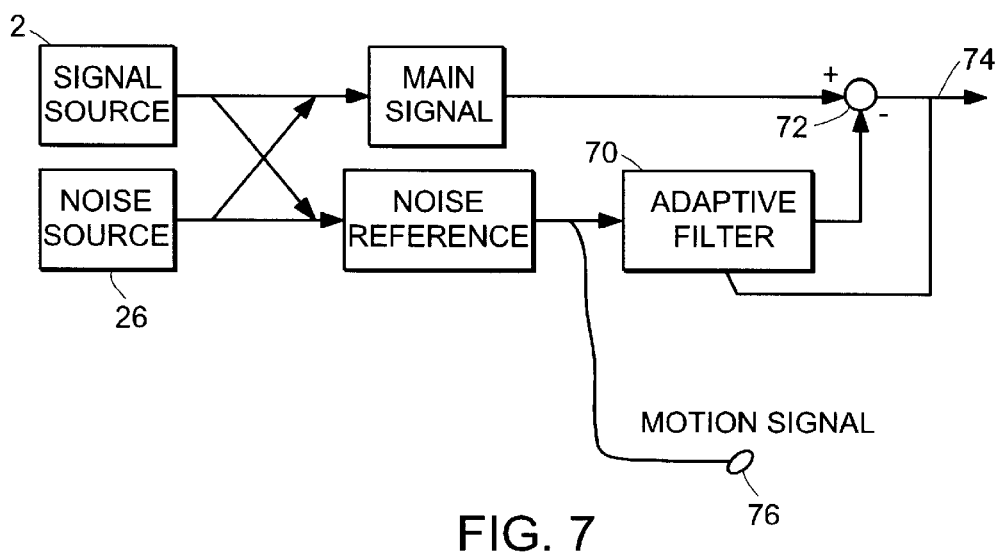
FIG. 7

PHOTOPLETHYSMOGRAPH SIGNAL-TO-NOISE LINE ENHANCEMENT

The present application is a Continuation-in-Part application of copending U.S. patent application Ser. No. 09/552,185, filed Apr. 18, 2000, and scheduled for issue, Jun. 11, 2002, as U.S. Pat. No. 6,402,690, which Application is incorporated herein by reference.

TECHNICAL FIELD

The present invention pertains to a device for monitoring the health status of a patient and, more particularly, for isolating such an apparatus from external disturbances.

BACKGROUND OF THE INVENTION

The present invention is an improvement upon finger-ring sensors such as those described in U.S. Pat. No. 5,964,701, issued Oct. 12, 1999, which patent is incorporated herein by reference. Finger-ring sensors may be employed, for example, for monitoring such physiological parameters as blood flow, blood constituent concentration, and pulse rate, all of which may be measured by other means that are more cumbersome, and thus less comfortable, to a patient.

Problems that arise in implementing a sensor that may be worn on a finger include issue of eliminating signal artifacts due to motion of the finger and of not interfering with blood circulation within the finger.

Devices have been advanced that employ a cuff for measuring the arterial pressure in a finger and thus provide ambulatory blood pressure monitoring. Such devices are described, for example, in Yamakoshi, et al., *Long-Term Ambulatory Monitoring of Indirect Arterial Blood Pressure Using a Volume-Oscillometric Method*, 23 Med. & Biol. Eng. & Comput., (1985), pp. 459–465 and in U.S. Pat. No. 4,539,997 (Wesseling et al.), which are incorporated herein by reference. In these devices, a cuff, encircling the finger, is inflated and pressure is applied uniformly around the finger, thereby interfering with the natural blood perfusion through the vasculature of the finger.

Another feature of some finger ring physiological monitoring systems is noise-cancellation, as taught, for example, in U.S. Pat. No. 6,263,222 (Diab et al.). This patent is also incorporated herein by reference. Diab teaches providing more than one source of light, with the different sources emitting at different wavelengths, for illuminating a single detector along different paths through the skin, and deriving two signals, one of which may be used to remove motion-induced artifacts from the other signal.

In addition to enhancing signal-to-noise in a photoplethysmograph without impeding blood flow through the finger, it would desirable to derive a separate signal that may be used for motion monitoring.

SUMMARY OF THE INVENTION

{The Invention Summary will comport with the claims as filed.}

BRIEF DESCRIPTION OF THE DRAWINGS

The invention will more readily be understood by reference to the following description taken with the accompanying drawings in which:

FIG. 6a is an exploded view of major components of a finger ring sensor in accordance with embodiments of the present invention, while FIG. 6b shows, in particular, a perspective view of the sensor band of FIG. 6a; and FIG. 7 is a schematic representation of adaptive filtering to remove motion artifacts on the plethysmograph signal, in accordance with embodiments of the present invention.

DETAILED DESCRIPTION OF PREFERRED EMBODIMENTS

Embodiments of the present invention provide improvements upon finger-ring sensors of the kind described in U.S. Pat. No. 5,964,701, and may also be applied to other sensors worn on the body for monitoring any of a variety of physiological parameters, including, without limitation, skin temperature, electrical impedance, pulse, blood constituent concentration, and/or blood flow.

Further description of embodiments of the invention is provided in Hutchinson, *Design and Signal Processing of Finger Photo Plethysmographic Ring Sensors for Reduced Motion Artifact and Circulation Interference*, Dissertation Submitted to the Massachusetts Institute of Technology, May, 2002, which is appended hereto and incorporated herein by reference.

In accordance with preferred embodiments of the invention, sensor data is transmitted to a computer through a wireless communication link and the patient status is analyzed continually and remotely. Abnormal health status and possible accidents may be detected by analyzing the sensor data. A sensor worn as a finger ring sensor has particular advantages since a ring sensor may be worn by the patient at all times, hence the health status may be monitored 24 hours a day. For purposes of the present description, the sensor will be referred to, without limitation, as a ring sensor, and the sensing modality, again without limitation, will be described in terms of a photoplethysmographic device for measuring a pulse using optical elements such as infrared light-emitting diodes (LEDs) and photodiodes.

Figure 1:
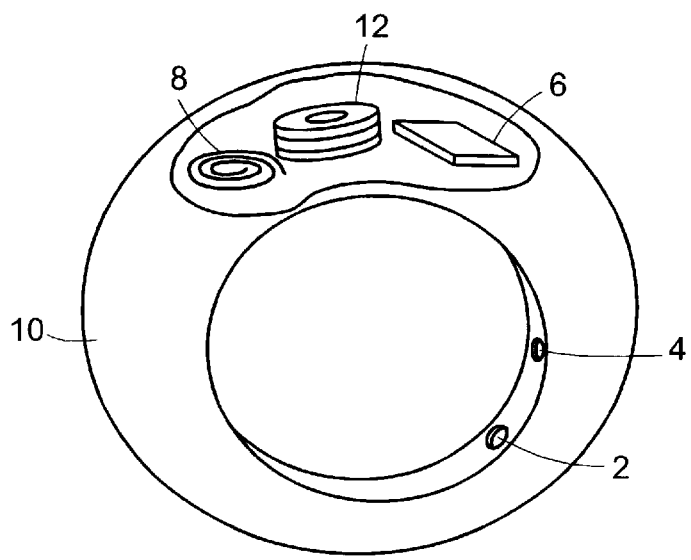
FIG. 1 is a perspective view of an embodiment of a ring sensor device to which the present invention may advantageously be applied.

A simple finger ring sensor to which the present invention may be advantageously applied is described with reference to FIG. 1. As shown in FIG. 1, one or more photo diodes 2 and one or more light-emitting diodes (LEDs) 4 are imbedded in a ring 10. The LEDs may emit light in the visible or infrared, and may be particularly chosen to emit light at one or more specified wavelengths, such as the isobestic wavelength discussed below. The pulse of the patient may be detected as a periodic change in the sensor output. Ring 10 may be placed on one of the fingers. In a preferred embodiment, ring 10 is placed on the middle finger, which is not only convenient for wearing the ring but also suitable for counting pulse.

The outer skin of the middle finger is thin, particularly at the sides of the finger, and a digital artery runs right beneath the thin skin. Light transmitted through the artery and detected by photodetector 2 generates a signal reflecting the volume of blood traversed. The detector signal is processed by controller 6 which may include a microprocessor, and the signal or data derived from it may be sent to a transmitter 8 for telemetry to a remote site, either on the patient's person or in the vicinity.

Figure 2:
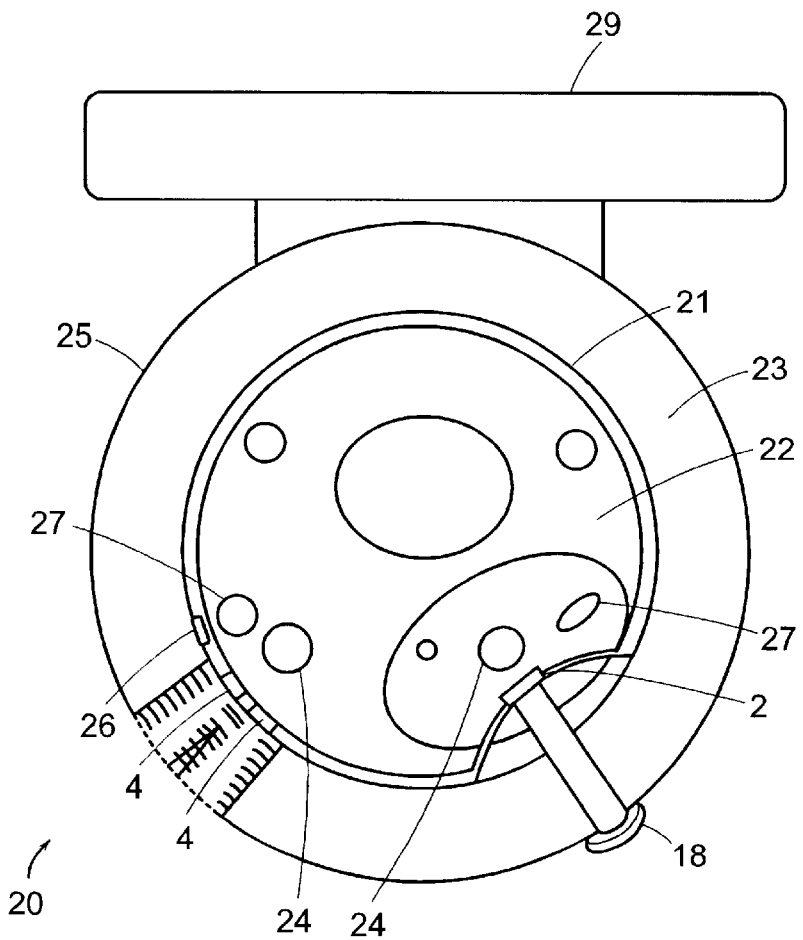
FIG. 2 is a cross-sectional view of a ring sensor embodying localized pressurization of the region of an artery, in accordance with an embodiment of the present invention.

Referring now to FIG. 2, a cross-section is shown of finger ring sensor 20 as worn on finger 22 of a patient. In preferred embodiments of the invention, a sensor band 21 is worn in direct contact with the finger and holds one or more detectors 2 and 26, against the skin of the finger. Sensor band 21 is encompassed by base ring 23 which, in turn, is encompassed by cover ring 25 which supports circuit module 29 containing battery 12, processor 6, and transmitter 8, all shown in FIG. 1, and serves also to shield detectors 2 and 26 from ambient light.

Arteries traversing the finger are designated generally by numeral 24, while numeral 27 denote veins. One or more light sources 4, such as LEDs, provide illumination, typically monochromatic, at one or more wavelengths. Photons from the LEDs pass through the skin. Although the photons illuminate in all directions, it is known that the average light path travels in a banana shape through a portion of the tissue and then back to the photodetector 2. Although, some scattered light escapes through the finger, the light of interest in the present description is absorbed by the tissue of the finger and by the photodetector 2. Light detected at photodetector 2 has periodic (AC) and constant (DC) components, with the constant component primarily governed by light source intensity, ambient light, detector sensitivity, soft tissue, bone, venous blood, capillary blood, and non-pulsatile arterial blood. The AC component, on the other hand, captures the pulsating arterial blood.

Figure 3A:
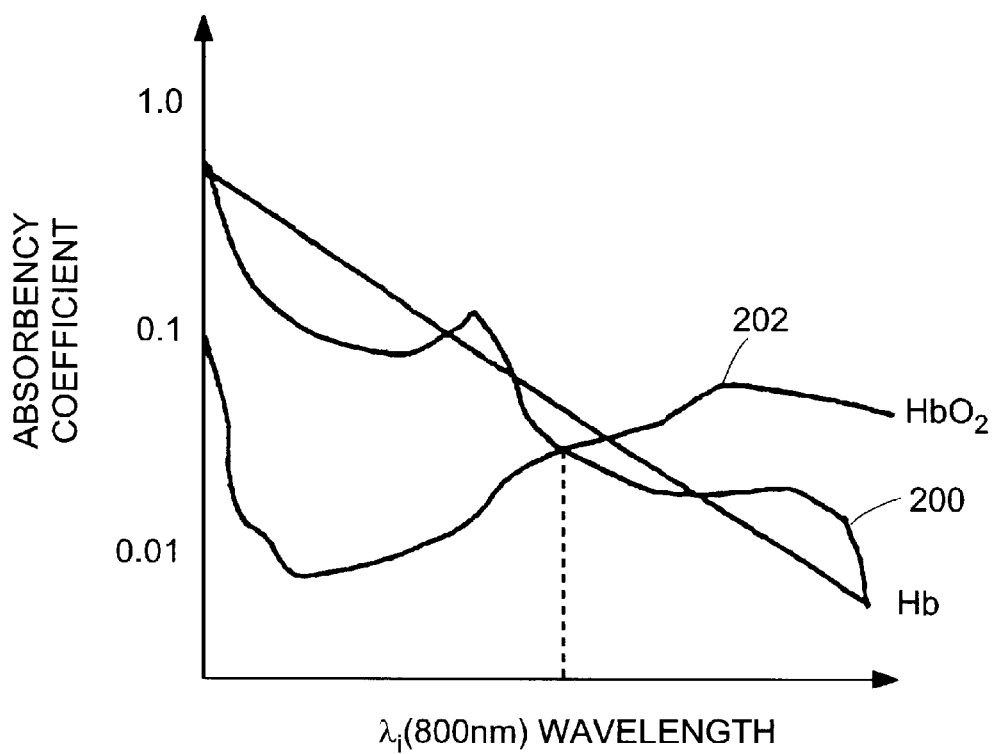
FIG. 3a shows plots of absorption spectra of hemoglobin and oxygenated hemoglobin for determination of blood constituent levels in accordance with an embodiment of the present invention.
Figure 3B:
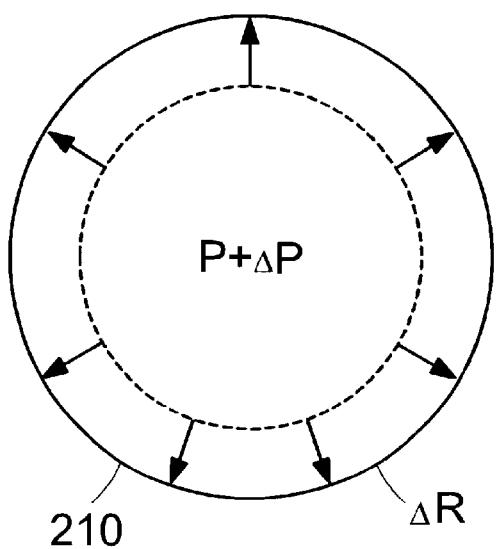
FIG. 3b is a schematic cross-section of a blood vessel showing the relationship between pressure, pressure increment, and radial increment.

In some embodiments of the invention, arterial blood flow and pressure are measured using LEDs emitting at the wavelengths specified with respect to the isobestic point of hemoglobin and oxygenated hemoglobin, at approximately 800 nanometers. In FIG. 3a, the absorption coefficients of hemoglobin 200 and oxygenated hemoglobin 202 are plotted as a function of wavelength $\lambda$. At the isobestic wavelength $\lambda_i$, the optical absorption is insensitive to the fraction of oxygenated hemoglobin. Thus, as shown in FIG. 3b, the aggregate arterial radial variation AR of artery 210 can be measured directly. Since arterial diameter, flow rate, and pressure are directly related, variation of the arterial diameter is proportional to changes $\Delta P$ in the arterial pulse pressure, so that the pulse may be measured with light emitted by LED 2 at the isobestic and detected by photo detector 4, without using a cuff.

Previous ring sensors have used an elastic band to secure the optical components to the skin. It is held in place by applying a sufficient amount of a uniformed external pressure around the finger, but avoids causing discomfort to the wearer. The dynamics of the arterial wall have been analyzed to determine the sufficient amount of pressure. It is known that as the blood travels throughout the body through a series of capillaries, veins, and arteries. Each vessel has certain pressure but differs depending on the location of the body. The arm has a typical blood pressure of approximately 120 mm Hg, while the finger has a blood pressure somewhat lower, in the vicinity of 100 mm Hg. These pressures can vary depending on the orientation of the particular body member. If the hand is raised or lowered, the internal blood pressure will be affected. This pressure, called the internal pressure, provides information regarding the health status of a patient.

Figure 4:
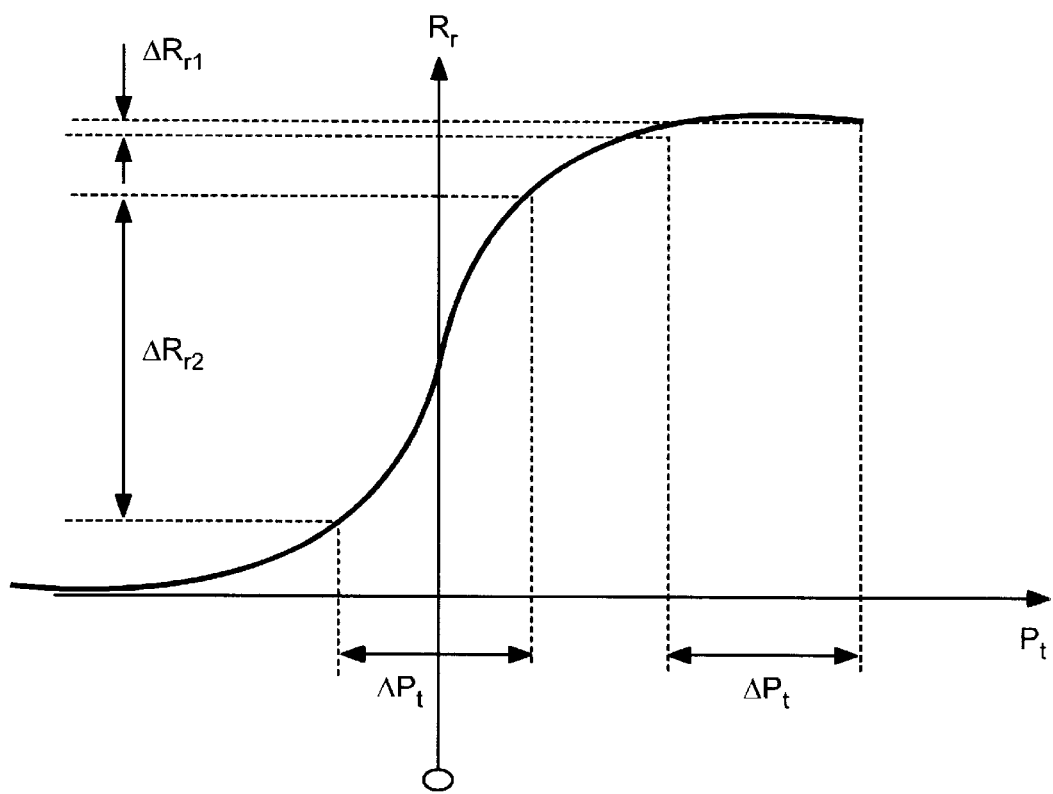
FIG. 4 shows a plot of arterial radius versus transmural pressure and operating points of optimal pressure bias and saturation in accordance with embodiments of the invention.

Knowledge of the blood pressure $P_i$ internal to a blood vessel and the external blood pressure $P_o$ provides the transmural blood pressure, given by the difference between the internal pressure $P_i$ and external pressure $P_o$. The transmural pressure of an artery is related to radius R of the artery as shown in FIG. 4. Typically, a small amount of external pressure applied to the finger produces a relatively small change in the radius of the artery, as show. If the external pressure is further increased such that the transmural pressure approaches zero, the radius is the unstressed radius, $R_r$. In addition, a small change in the transmural pressure around zero, yields a large change in radius of the artery. This is due to the non-linear behavior of the arterial wall compliance, i.e. the slope of the radius-transmural pressure curve in FIG. 4. Note that the compliance becomes maximized near the zero transmural pressure.

Figure 5:
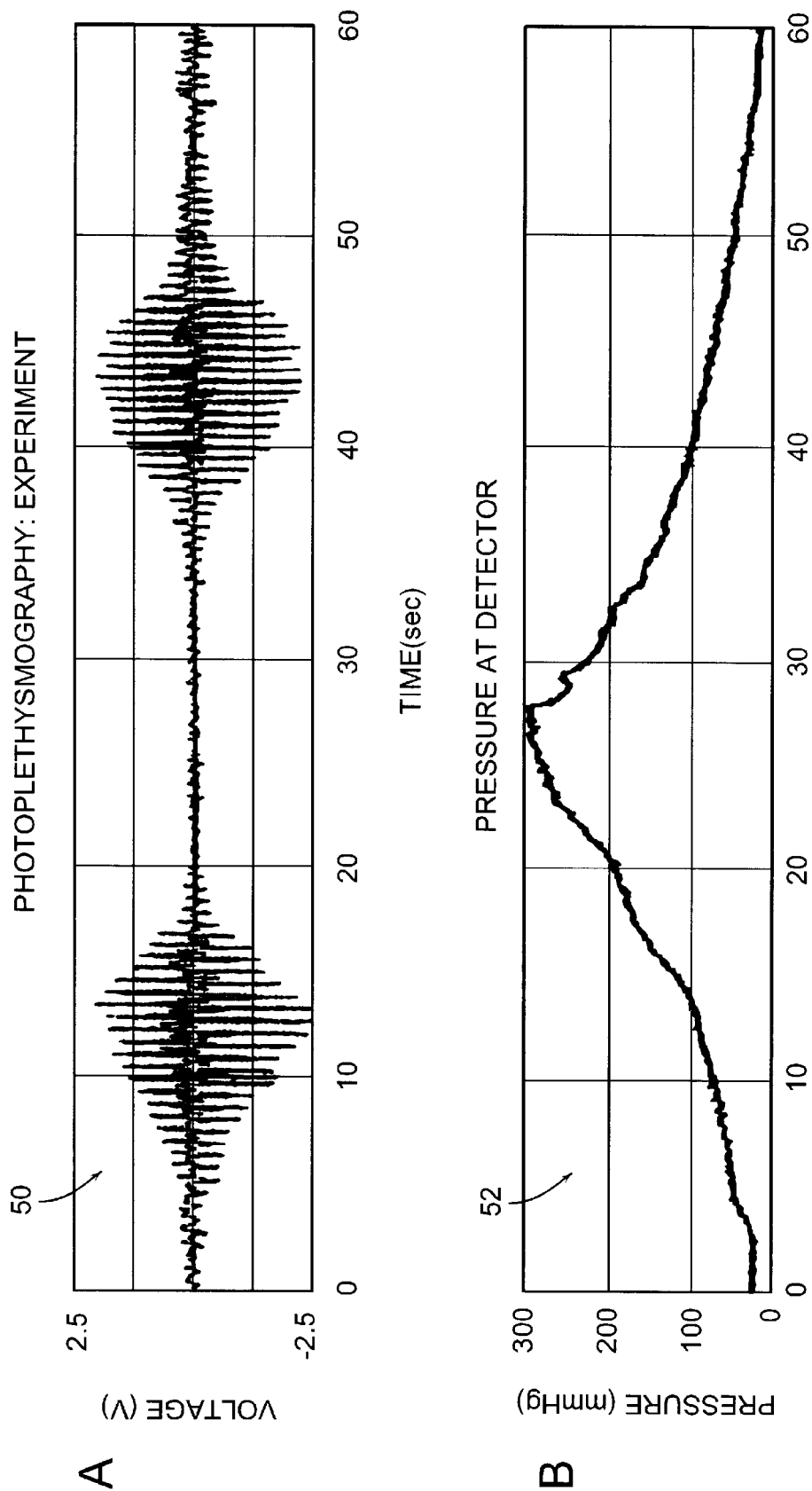
FIG. 5 shows the response of a ring sensor, in accordance with an embodiment of the present invention, in the face of applied local pressurization bias.

For a fixed sampled length of artery, the sampled volume of the blood in the artery is proportional to the square of the radius. Thus, as a result of the radius increasing, the blood volume increases, which causes the volumetric arterial pulsations to increase. If the external pressure is further increased, the transmural pressure decreases, which causes the artery to occlude. If an external force is further applied, complete occlusion develops. Thus, preferably, enough pressure is applied to improve the plethysmographic signal, but it is undesirable that enough pressure be applied to cause occlusion of the artery, or of other vasculature in the finger. FIG. 5 shows the measured photoplethysmographic signal 50 as the circumferential pressure 52 about the finger is increased and then decreased.

If the entire circumference of the finger is pressurized to the point of pinching, both pressure sores, and attendant tissue necrosis, as well as collapse of other blood vessels, such as veins and capillaries within the finger, may ensue interfering with healthy blood perfusion of the finger. In particular, the vein typically collapses at a transmural pressure approximately 20–30 mm Hg.

In order to selectively increase the external pressure at the artery of interest thereby increasing the transmural pressure to the point of optimal plethysmographic signal, without causing occlusion of other vasculature within the finger, a localized pressure is applied, in accordance with preferred embodiments of the present invention, and locally adjusted as by adjuster 18 shown in FIG. 2.

In accordance with an embodiment of the invention, finger ring 10 has components as shown in the exploded depiction of FIGS. 6a and 6b.

Lightweight cover 25 is preferably made of cast acrylic. The inner diameter widens to couple to base unit. The main function of the cover is to protect the sensors from outside elements. Also, it reduces the influence of external forces. Being decoupled from the sensor band 21, a direct force on the surroundings of the sensors will not affect the output of the signal. In addition, the cover unit serves in limiting saturation stemming from ambient light.

Base unit 23 is preferably made of the same cast acrylic material as cover 25 and is toleranced to provide a secure fit by means of friction. The base unit 23 may advantageously elastic sensor band 21 to rotational motion only. This component also manages small wires stemming from the signal-processing unit to various sensors located on the sensor unit. Moreover, this component aids in shielding the ambient light, which the cover unit could not handle.

An adjustable band 21 is used (rather than a tight elastic band) for supporting one or more detectors and one or more light sources against the finger of the user. Adjustability provides for use on fingers of various sizes and may advantageously also lower the occurrence of necrosis. Sensor band 21 retains photodetector 2 and the two LEDs 4, which together provide photoplethysmographic response.

Because sensor band 21 is loose, optical components 2 and 4 are not secured around the finger base. Pressure member 60, also referred to herein as an 'adjuster', provides contact between the photodetector and the skin. Adjuster 60 places pressure directly on the finger base, by adjustment of pressure in a direction substantially normal to the finger and similarly normal to the ring. In addition, the adjuster can tune the pressure applied such that the transmural pressure on a specified blood vessel approaches zero to provide an improved signal. Setting the local pressure to a preferred level is referred to herein as 'biasing' the pressure. A setscrew may used for this application such that it is hidden from the view for aesthetic purposes as may any other mechanical device providing for application of local pressure. Since blood perfusion to the fingers is plethoric, substantial reduction in the arterial blood flow is possible without seriously disrupting perfusion to the tissue of the finger, indeed, only 25–30% of the normal blood flow is typically needed.

Pressure band 62, preferably fabricated from an elastomeric material such as rubber, serves to alleviate direct stress on photodetector 2. Without the pressure band, applying pressure directly on the photodetector may induce localized stress fractures in the photodetector. A pressure band applies pressure not only to the photodetector, but a small area around the photodetector, thus increasing the size of the region where adjuster 60 may function effectively. Use of a pressure band or other means for distributing the pressure applied by the adjuster 60 is not essential to practice of the invention but is within its scope as claimed.

Finally, in the embodiment of FIG. 6*b*, a second photo plethysmographic sensor 26 is added to the sensor band 21 to provide a means detecting motion. Photodetector 26 is non-collocated with photodetector 2, and, in a preferred embodiment, is located approximately 90 degrees away from the location of the first photodetector 2. By using the information of the provided by an LED source 4 emitting light at approximately 660 nm, venous contribution to a detected plethysmographic signal can be measured. Because the vein is more susceptible to artifacts due to flexure or other motion of the finger, the venous contribution permits motion detection. Since the band 21 has been modified such that the vein is not occluded and the location of the sensor prohibits local occlusion, a reliable plethysmographic detection system is made possible.

A major source of interference with sensor readings in wearable physiological sensors is that of artifacts induced in the signal train by motion of the patient. In accordance with a preferred alternate embodiment of the invention, motion artifacts are reduced or eliminated by using one or more auxiliary sensors 26 to detect body motion. In the embodiment discussed with reference to FIG. 2, sensor 26 is a photodetector, though other sensors may be used to detect finger motion including an accelerometer and a microelectromechanical systems (MEMS) accelerometer, in particular. By virtue of being disposed at a location distinct from that of sensor 2, while sensor 2 measures the response of an artery particularly pressurized to increase the AC component of a signal due to radial response to arterial pulsation, the signal derived by sensor 26 samples veins and thus blood vessels containing a large volume of blood at a low pressure. The signal due to sensor 26 is thus especially sensitive to motion of the entire finger and is useful for monitoring activity level of the patient.

Techniques of adaptive digital filtering are then used to eliminate motion artifacts in the signal train. As shown schematically in FIG. 7, in adaptive noise cancellation, adaptive filter 70, which, in a preferred embodiment is a digital filter, adaptively eliminates interference due to the motion artifact by removing, by means of summer 72, the motion signals from the sensor signals. In addition to providing a signal output 74 from which motion artifacts have been removed, the reference signal technique taught by the present invention also separately provides a motion signal output 76 that may advantageously provide a separate measure of wellness of the patient.

The described embodiments of the invention are intended to be merely exemplary and numerous variations and modifications will be apparent to those skilled in the art. All such variations and modifications are intended to be within the scope of the present invention as defined in the appended claims.

We claim:

1. In a photoplethysmograph for characterizing blood volume of the type having a light source and a detector disposed about a region of body tissue containing a specified blood vessel carrying a blood flow characterized by an internal pressure, an improvement comprising a pressure member for selectively applying an external pressure to the specified blood vessel in such a manner as substantially to balance the internal pressure of the blood flow.

2. A photoplethysmograph in accordance with claim 1, wherein the pressure member is disposed in such a manner as to apply pressure in a direction substantially normal to the body tissue.

3. In a photoplethysmograph for characterizing blood volume of the type having a light source and a detector disposed about a finger, the light source and a detector coupled to a ring for encircling the finger, an improvement comprising a pressure member for selectively applying external pressure to the specified blood vessel.

4. A photoplethysmograph in accordance with claim 3, wherein the pressure member is disposed in such a manner as to apply pressure in a direction substantially normal to the ring.

5. A photoplethysmograph in accordance with claim 3, wherein the pressure member is a set screw.

6. A monitoring system for monitoring a physiological characteristic of a patient, the monitoring system comprising:
   a. a source of light disposed proximately to a region of body tissue of the patient;
   b. at least one sensor for providing a signal based on detection of light through a specified blood vessel of the body tissue, the specified blood vessel carrying a blood flow characterized by an internal pressure; and
   c. a pressure member in contact with and not encircling the region of body tissue for applying pressure through the region of tissue to the specified blood vessel in such a manner as substantially to balance the internal pressure of the blood flow.

7. In a photoplethysmograph for characterizing blood volume of the type having a first light source and a detector disposed about a region of body tissue containing a specified blood vessel, an improvement comprising a motion reference signal generator, the motion reference signal generator comprising:

a. a second light source disposed substantially proximally to the body tissue; and b. a second detector located at a position distinct from that of the first detector for generating a motion signal.

8. A photoplethysmograph in accordance with claim 7, wherein the second detector is a photodetector for characterizing transmission through body tissue of illumination by the second light source.

9. A photoplethysmograph in accordance with claim 8, wherein the first and second light sources are identical.

10. A photoplethysmograph in accordance with claim 8, wherein the first and second light sources emit light having distinct spectral characteristics.

11. A method for obtaining contemporaneous plethysmographic and motion data with respect to a body member, the method comprising;

a. encircling the body member with a ring having at least one light source and at least two detectors;

b. deriving a plethysmographic signal from the first detector based on light transmission along a first path including a specified blood vessel; and c. deriving a motion signal from the second detector based on light transmission along a second path.

* * * * *

UNITED STATES PATENT AND TRADEMARK OFFICE
CERTIFICATE OF CORRECTION

PATENT NO.     : 6,699,199 B2
DATED          : March 2, 2004
INVENTOR(S)    : Haruhiko H. Asada et al.

It is certified that error appears in the above-identified patent and that said Letters Patent is hereby corrected as shown below:

<u>Title page,</u>
Item [54], Title, replace "PHOTOPLETHYSMOGRAPH SIGNAL-TO-NOISE LINE ENHANCEMENT" with -- PHOTOPLETHYSMOGRAPH SIGNAL-TO-NOISE ENHANCEMENT --.
Item [75], Inventor, please add -- Sokwoo Rhee --

Signed and Sealed this

Fourth Day of May, 2004

JON W. DUDAS
*Acting Director of the United States Patent and Trademark Office*